US007028927B2

(12) United States Patent
Mermet

(10) Patent No.: US 7,028,927 B2
(45) Date of Patent: Apr. 18, 2006

(54) FLOWRATE CONTROL DEVICE, IN PARTICULAR FOR MEDICAL USE

(75) Inventor: Bernard Mermet, Matafelon-Granges (FR)

(73) Assignee: Sobem, Arbent (FR)

( * ) Notice: Subject to any disclaimer, the term of this patent is extended or adjusted under 35 U.S.C. 154(b) by 113 days.

(21) Appl. No.: 10/496,978

(22) PCT Filed: Dec. 6, 2002

(86) PCT No.: PCT/FR02/04217

§ 371 (c)(1),
(2), (4) Date: May 27, 2004

(87) PCT Pub. No.: WO03/047660

PCT Pub. Date: Jun. 12, 2003

(65) Prior Publication Data

US 2004/0261872 A1    Dec. 30, 2004

(30) Foreign Application Priority Data

Dec. 6, 2001    (FR) .................................. 01 15794

(51) Int. Cl.
*B05B 1/30* (2006.01)

(52) U.S. Cl. ..................... 239/569; 239/571; 239/568; 239/537; 239/538; 239/451; 239/460; 137/556; 604/32; 604/246; 604/248; 604/149.1; 251/208; 251/209; 251/309; 383/106

(58) Field of Classification Search ................ 239/568, 239/571, 537, 538; 137/556; 604/246, 248, 604/149.1; 383/106
See application file for complete search history.

(56) References Cited

U.S. PATENT DOCUMENTS

| 4,335,729 | A | * | 6/1982 | Reynolds et al. ........... 600/487 |
| 5,005,604 | A | * | 4/1991 | Aslanian ..................... 137/556 |
| 5,113,904 | A | * | 5/1992 | Aslanian ..................... 137/556 |
| 5,875,889 | A | * | 3/1999 | Albisetti ..................... 206/221 |
| 6,156,025 | A |   | 12/2000 | Niedospial, Jr. et al. |
| 6,916,010 | B1 | * | 7/2005 | Beck et al. ................. 251/209 |
| 2003/0105448 | A1 | * | 6/2003 | Shiraishi et al. ............ 604/415 |

FOREIGN PATENT DOCUMENTS

WO    WO 02/15965  A2    2/2002
WO    WO 02/015965 A3    2/2002

* cited by examiner

*Primary Examiner*—David A. Scherbel
*Assistant Examiner*—James S. Hogan
(74) *Attorney, Agent, or Firm*—Oliff & Berridge, PLC

(57) ABSTRACT

The invention concerns a device comprising two components connected to each other with possible displacement of one component relative to the other, sealing means arranged between said two components, and flow rate adjusting means actuated by displacement of one component relative to the other. The invention is characterized in that the device comprises positioning means for placing the two components in two different positions, namely a first so-called sterilizing position, wherein said two components do not, or hardly exert, any stresses on the sealing means, and second so-called operating position, wherein said two components stress the sealing means to provide the required sealing conditions.

9 Claims, 5 Drawing Sheets

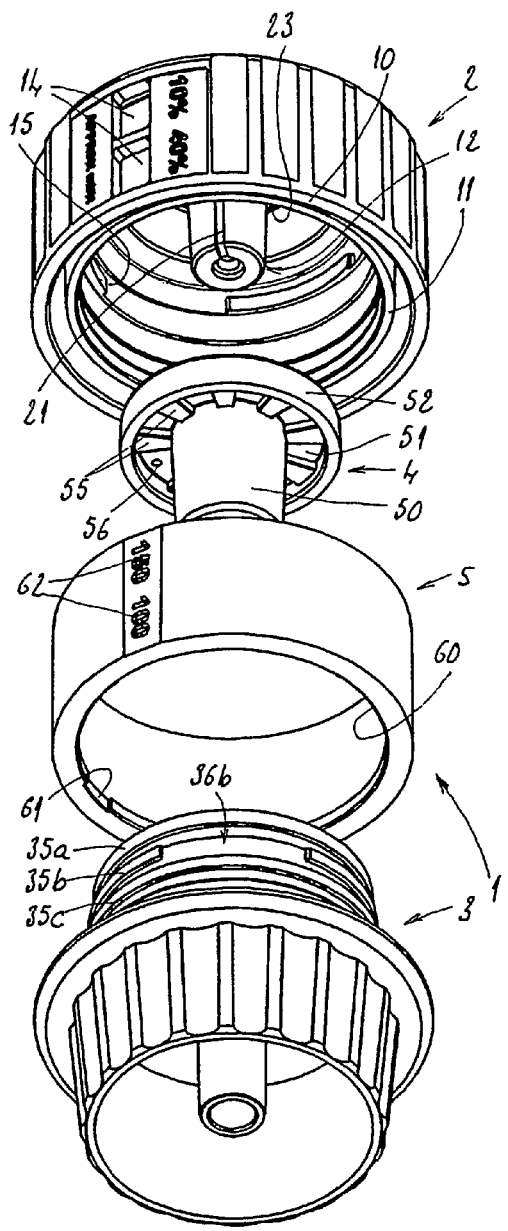
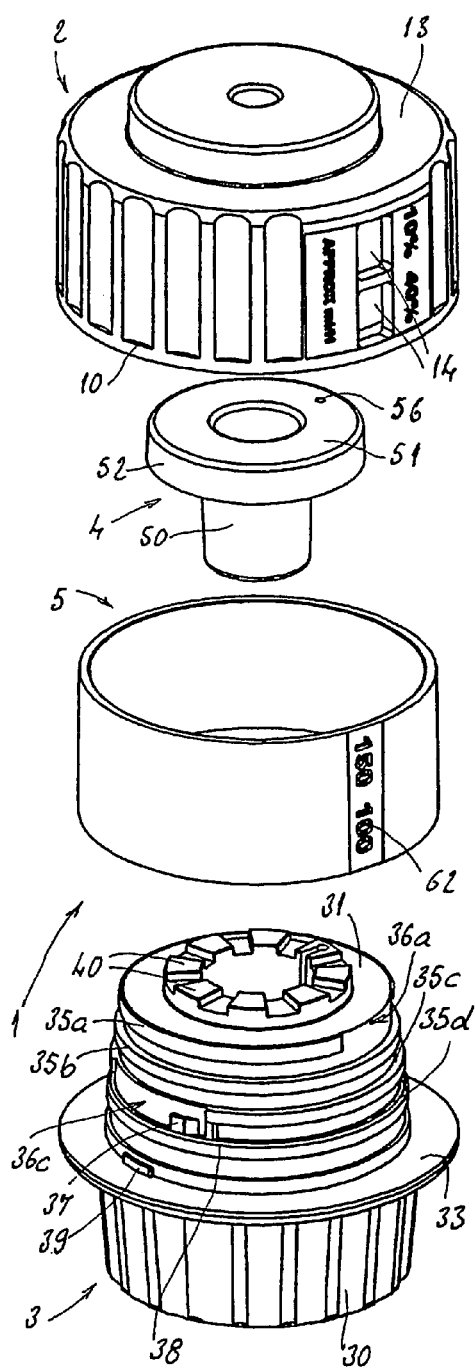

FIG 5
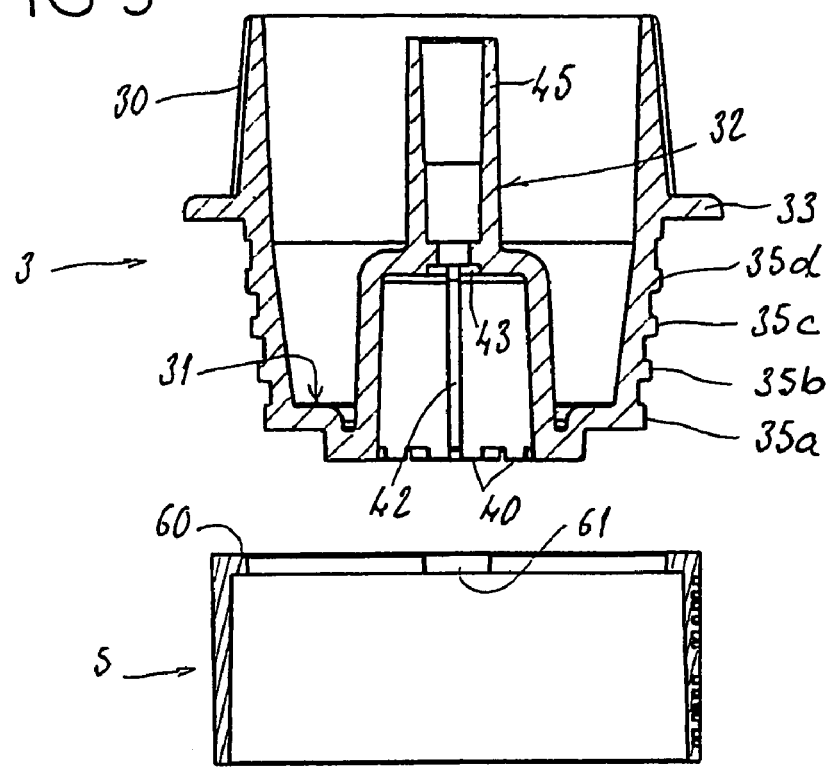
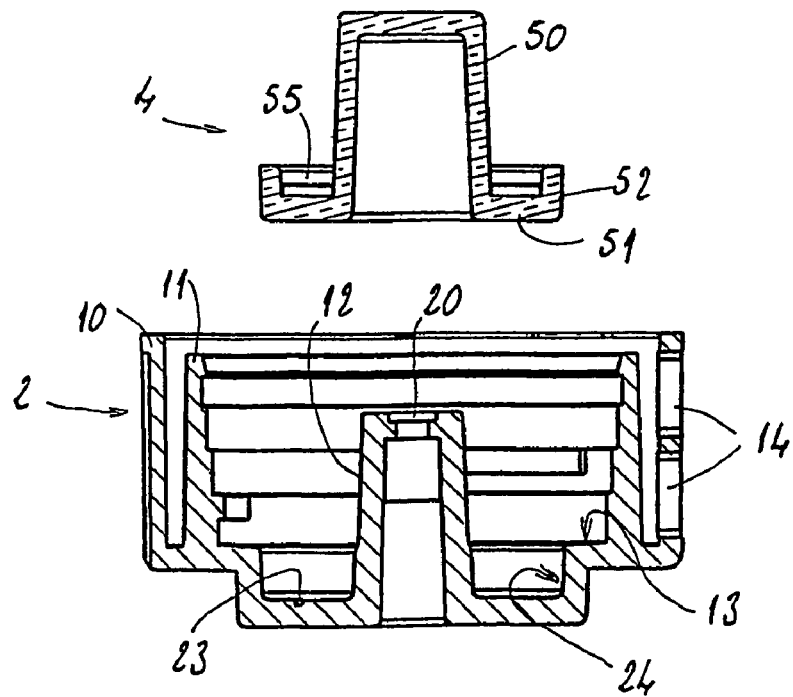

FLOWRATE CONTROL DEVICE, IN PARTICULAR FOR MEDICAL USE

The present invention relates to a flowrate control device, in particular for medical use.

Such a device is presently used in particular in infusion systems for controlling the flowrate of the infused liquid.

Flowrate control is to be understood in the broad sense of the term and also concerns flow distributors with one or more valves and with opening and closure functions.

A known device comprises two components connected to one another pivotably, one of which delimits a conduit intended to be connected to a source of fluid, in particular a bag of liquid for infusion, and of which the other delimits a conduit intended to be connected to a tube for delivery of the liquid.

In one configuration, one of said components comprises a base in which there is formed, coaxially with respect to the axis of pivoting of one component relative to the other, a circular groove extending along slightly less than one turn and having a variable depth along its length; the conduit formed in this component opens into this groove. The other component is integral in rotation with a sealing washer made of resilient material, having an orifice communicating on the one hand with the conduit of this other component and on the other hand with said circular groove.

The pivoting of this other component relative to the first component mentioned permits displacement of the orifice of the sealing washer along the groove and, consequently, on account of the different depth of this groove at different locations thereof, permits variation of the cross section of the fluid delivery conduit depending on the angular position of one component relative to the other.

When the required sealing is obtained, the washer is clamped tight between the two components of the device, with the result that quite substantial stresses are generated on this washer.

These stresses prohibit steam sterilization of the device. The reason is that the increase in temperature would lead to a softening of the material constituting said components and, also, said washer, and, in view of the aforementioned stresses, there would be a risk of these materials exhibiting creep, which would adversely affect the leaktightness and functioning of the device, or could even risk rendering the device inoperative.

For this reason, a device of this type is presently sterilized either by particle radiation or by means of a gas permitting low-temperature sterilization, for example ethylene oxide.

The main disadvantage of these methods of sterilization is that they necessitate strict safety measures and are therefore relatively complex to perform. The use of a low-temperature sterilization gas also has the disadvantage of disseminating chemical products into the environment.

According to another design, the sealing of the device is obtained by two conical components which bear against one another with pressure. In this case too, sterilization poses a problem because the plastic components have a tendency to exhibit creep under stress, which subsequently results in defective sealing.

The invention aims to overcome these disadvantages by making available a control device which can be sterilized by steam.

It is also an object of the invention to make available a control device which provides perfect sealing and has an optimized structure from the point of view of its manufacture.

The device according to the invention comprises, in a manner known per se, two components connected to one another with possibility of displacement of one component relative to the other, sealing means placed between these two components, and flowrate control means actuated by the displacement of one component relative to the other.

According to the invention, the device comprises positioning means allowing the two components to be placed in two different positions, namely a first position, called the "sterilizing" position, in which these two components do not exert, or hardly exert, any stresses on the sealing means, and a second position, called the "operating" position, in which these two components stress the sealing means in such a way as to obtain the required sealing.

The two components of the device are placed in the "sterilizing" position at the time of sterilization of the device, in order to cancel all the stresses to which these components are subjected when they clamp the sealing member in order to obtain the required sealing. It then becomes possible to sterilize this device with steam, without the heating which results from this type of sterilization causing any risk of creep of the material from which these components and the sealing member are made. Such sterilization is thus made possible without adversely affecting the sealing and functioning of the device.

Preferably, said positioning means comprise:
at least one groove formed in one of said components;
at least one boss integral with the other component and sliding in this groove in order to permit displacement of the components relative to one another; and
at least one clearance communicating with the groove, in which clearance the boss can be engaged in order to permit displacement of the component comprising the groove relative to the component comprising the boss, from said operating position to said sterilizing position, and vice versa.

This displacement is thus made possible in a way which is simple to manufacture and practical to use.

Advantageously, each groove and/or each boss has inclined zones forming ramps, these ramps facilitating the movement of the components from the sterilizing position to the operating position counter to the elastic restoring force of the sealing means.

According to a preferred embodiment of the invention, when the device comprises at least one groove and at least one boss as mentioned above, the groove has at least one entry in which a boss can be engaged in a defined position of one component relative to the other, and one of the components comprises at least one immobilizing catch, while the other component comprises at least one corresponding immobilizing catch, these catches being configured in such a way that the catch or catches of one component can snap in beyond the catch or catches of the other component during the first displacement of one component relative to the other and can then be immobilized beyond these in such a way as to prevent any return of the components to the position in which each boss is situated opposite each entry.

The device can thus be assembled in a way which is particularly simple and easy to perform.

According to one embodiment, the sealing means placed between the two components (2, 3) are formed by a separate sealing member (4).

Preferably, the sealing member has a sealing portion with a U-shaped cross section, and said components have shapes which are such that, when they are joined together, they enclose this sealing portion from all directions.

Perfect sealing is thus obtained.

According to a preferred embodiment of the invention, said components are connected pivotably to one another, and one of the components delimits a conduit intended to be connected to a source of fluid, while the other component delimits a conduit intended to be connected to a tube for delivery of said fluid; one of said components comprises a wall in which there is formed, coaxially with respect to the axis of pivoting of one component relative to the other, a circular groove which extends along lightly less than one turn and has a variable depth along its length, and the conduit formed in this component opens into this groove; the other component is integral in rotation with the sealing member which has an orifice communicating on the one hand with the conduit of this other component and on the other hand with said circular groove; the pivoting of this other component relative to the first component mentioned permits displacement of the orifice of the sealing member along the groove and, consequently, on account of the different depth of this groove at different locations thereof, permits variation of the cross section of the fluid delivery conduit depending on the angular position of one component relative to the other.

One of the components of the device can comprise at least one slot opening to the outside, and the other component of the device can be integral in rotation with a ring which comprises data relating to the flowrate controlled by means of the device, said data coming into line with said slot in the different angular positions of the component integral with the ring relative to the component comprising the slot.

According to one embodiment, the sealing means are formed by two complementary conical surfaces which bear against one another and belong respectively to the components (2, 3).

To ensure that it is clearly understood, the invention is again described below with reference to the attached diagrammatic drawing which shows, as non-limiting examples, two embodiments of the device according to the invention.

FIG. 1 is a perspective view of the components of a flowrate control device, before assembly;

FIG. 2 is a perspective view of these components at another angle;

FIG. 5 is a view of the components, in a cross section passing through the axis of these components, before assembly.

FIGS. 1 to 6 show a flowrate control device 1 for medical use.

Figure 3:
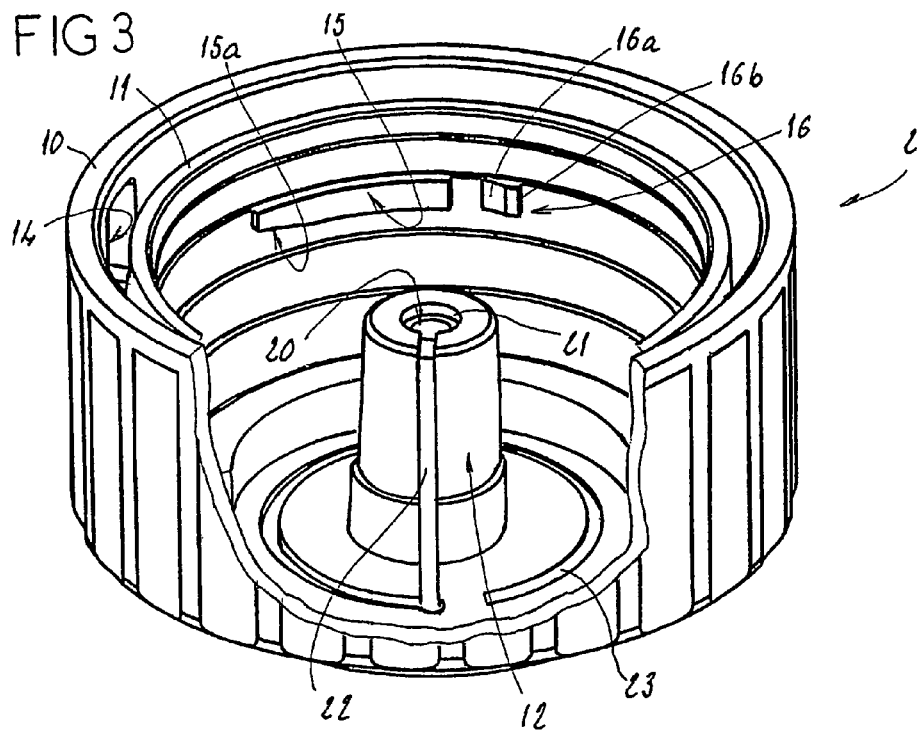
FIG. 3 is a perspective view, on an enlarged scale, of one of its components, with part cut away.

This device 1 comprises a first component 2, a second component 3 intended to be connected pivotably to the component 2, a sealing member 4, and a ring 5.

The component 2 comprises an outer peripheral wall 10, an inner peripheral wall 11, a hollow central stub 12, a base 13, two slots 14 formed in the wall 10, three bosses 15 projecting radially inward from the inner face of the wall 11, and an immobilizing catch 16 also projecting radially inward from this same internal face.

The wall 10 has anti-slip contours on its outer face.

As the figures show, the wall 11 is formed at a distance from the wall 10, so that these walls 10, 11 delimit between them an annular space in which the ring 5 can be engaged and can pivot.

The stub 12 is arranged coaxially with respect to the component 2. It is evident more particularly from FIG. 3 that it has an axial hole 20 communicating, via a circular groove 21 and a longitudinal groove 22, with a circular groove 23 formed in the base 13, coaxially with respect to the stub 12. It is evident from FIG. 3 that this groove 23 extends along slightly less than one turn and that it has a variable depth along its length.

The hole 20 communicates with the space delimited internally by the stub 12, which itself opens to the outside of the component 2.

FIG. 5 shows that the base 13 forms a circular recess 24 around the stub 12.

The bosses 15 are arranged at 120 degrees to one another and are situated at three different heights of the wall 11. They have indented zones at their edges directed toward the base 13 and in the area of one of their ends, these zones thus forming inclined walls 15a.

The catch 16 is formed near the stub 15 situated highest, at the side thereof remote from the end having the wall 15a. This catch 16 is configured to permit snap-fitting, that is to say has an inclined wall 16a and a wall 16b oriented radially.

The component 3 comprises a peripheral wall 30, a base 31, and a hollow central stub 32.

The wall 30 has a flange 33 protruding from its outer face, substantially at half the height of the latter, this flange 33 being intended to bear against the upper edge of the wall 10 when the components 2 and 3 are joined to one another.

This flange 33 delimits an "outer" part of the wall 30, that is to say situated outside the device 1 after assembly of the latter, and an "inner" part of this wall 30, that is to say intended to be engaged in the component 2.

The outer part has anti-slip contours on its outer face.

The inner part comprises ribs 35a, 35b, 35c, 35d which project radially outward and between them define three superposed channels. The rib 35a nearest the base 31 is interrupted over an angular distance greater than the angular length of a boss 15, thus delimiting a zone 36a of entry of one of these bosses 15 into the channel nearest the base 31. The rib 35b is interrupted in the same way over an angular distance greater than the angular length of a boss 15, but at a location offset by 120 degrees relative to the zone of entry 36a, thereby delimiting a zone of entry 36b of one of the bosses 15 into the intermediate channel. In the same way, the rib 35c is interrupted over an angular length greater than the angular distance of a boss 15, but at a location offset by 120 degrees relative to the zone of entry 36b, thereby delimiting a zone 36c of entry of one of the bosses 15 into the channel farthest from the base 31.

The wall 30 additionally comprises a snap-fit catch 37 and a positioning limit stop 38, being an upward continuation of the adjacent end of the rib 35c. The inclined wall 37a of the catch 37 is directed toward the limit stop 38.

Below the flange 33, the component 3 comprises a stud 39 projecting radially outward.

The base 31 comprises a ring of radial crenelations 40 projecting axially from its outer face.

Figure 4:
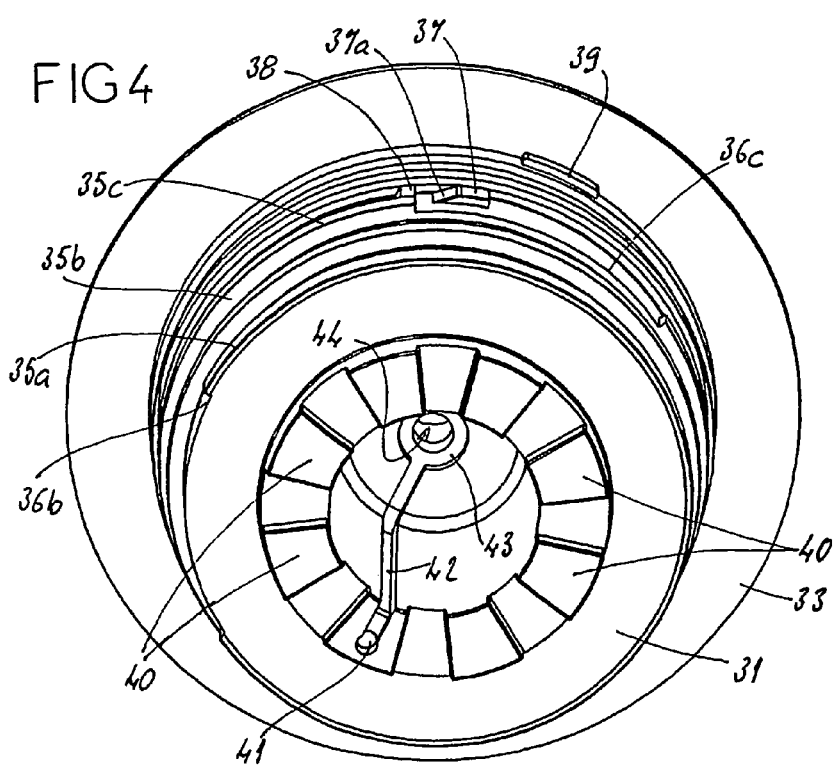
FIG. 4 is a perspective view of another of its components, again on an enlarged scale.
Figure 6:
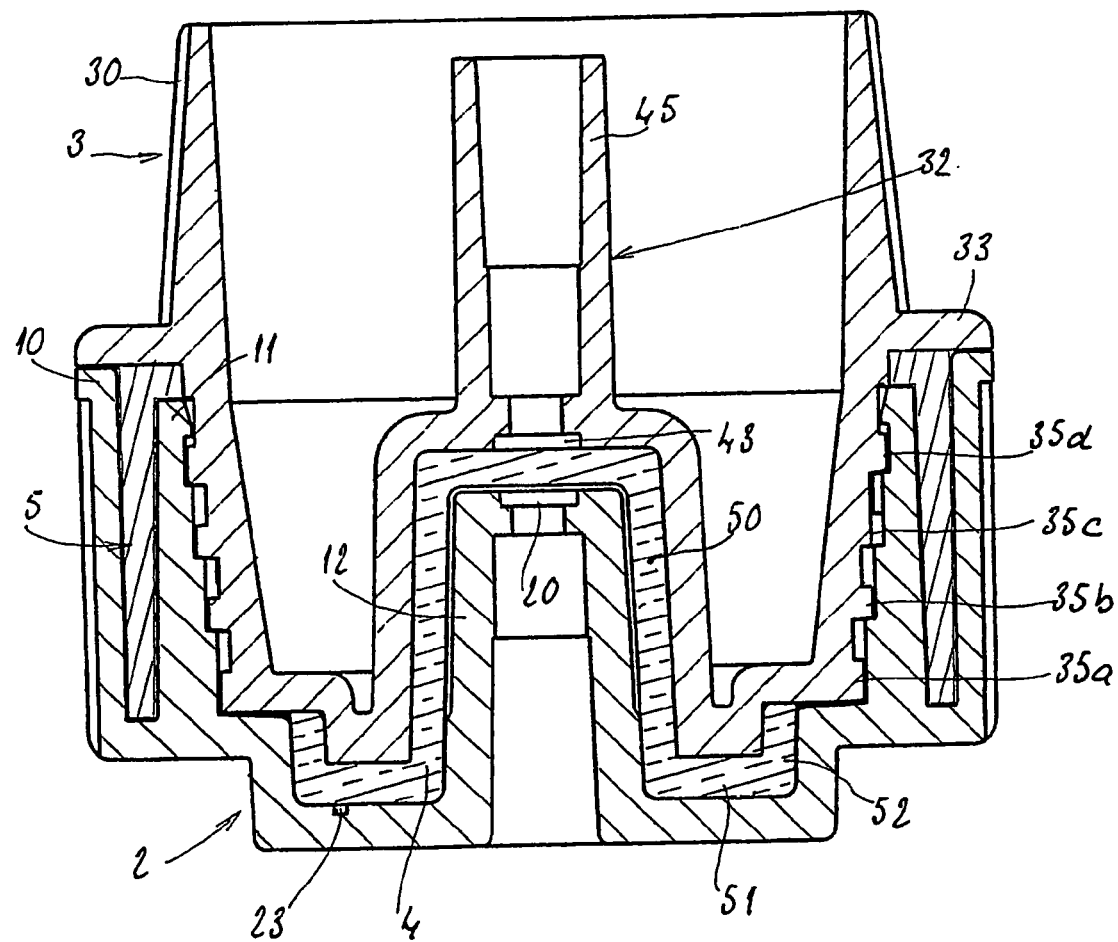
FIG. 6 is a similar view to FIG. 5, on an enlarged scale, after assembly of said components.

In addition, as is shown more particularly in FIG. 4, the base 31 has a hole 41 passing through it, connected, via a longitudinal groove 42 and a circular groove 43, to an orifice 44 formed in a shoulder of the stub 32. The distance of the hole 41 from the axis of revolution of the component 3 corresponds to the radius of the circular groove 23, so that this hole 41 is situated opposite this groove 23 and can travel the latter when the component 3 is pivoted with respect to the component 2.

The stub 32 is formed coaxially with respect to the component 3. Beyond the wall forming the aforementioned shoulder, it has a connection nozzle 45, for example of the Luer type, projecting opposite the base 31.

The sealing member 4 is made of a resilient material such as a silicone. It has a hollow central stub 50, a base 51, and a raised peripheral edge 52.

The stub 50 is dimensioned externally to engage tightly in the lower part of the stub 32 and is dimensioned internally to be engaged on the stub 12 with the possibility of pivoting relative to the latter.

The base 51 has radial crenelations 55 able to engage tightly in the spaces delimited by the crenelations 40, and vice versa, so as to ensure a rotational connection between this member 4 and the component 3. The dimensions of this base 51, and those of the peripheral edge 52, are such that this base 51 and this edge 52 can be engaged tightly in the circular recess 24, but with the possibility of pivoting relative to the component 2.

This base 51 comprises a hole 56 which comes into line with the hole 41 when the member 4 is joined to the component 3.

The ring 5 has a rim 60 projecting radially inward, and a notch 61 formed in this rim 60. This rim 60 permits engagement of the ring 5 on the wall 30 until engagement of the stud 39 in the notch 61, which ensures rotational wedging of this ring 5 in relation to the component 3.

The ring 5 additionally comprises a series of data items 62 relating to the flowrate which can be controlled by the device 1, said data being printed on its outer face, and which data comes into line with the slots 14 in the different angular positions of the component 3 relative to the component 2. These data 62 thus inform the user of the controlled flowrate.

The device 1 is assembled by engaging the member 4 on the component 3, engaging the ring 5 in the circular space delimited by the walls 10 and 11, then engaging the assembly of component 3/member 4 in the component 2, with the bosses 15 situated opposite zones 36a to 36c. In the area of the zone 36c, the limit stop 38 directs the catch 16 into the space delimited between this limit stop 38 and the inclined wall 37a of the catch 37. When the component 3 is pivoted with respect to the component 2 in the clockwise direction in the example represented in the figures, the inclined walls 16a and 37a of the catches 16 and 37 slide on one another, which, by elastic deformation of the component 3, causes the catch 16 to pass beyond the catch 37 and be locked behind it. The assembly of components 3 and 2 has thus been made irreversible.

In this state of assembly, the orifice 20, the grooves 21, 22 and 23, the holes 56 and 41, the grooves 42 and 43, and the orifice 44 delimit a conduit passing right through the device 1. The base of the component 2 can be connected to a source of liquid for infusion, for example a flexible bag, and the nozzle 45 can be connected to a tube for delivering the liquid to a patient.

The pivoting of the component 3 relative to the component 2 makes it possible to displace the hole 56 along the groove 23 and thus to vary, according to the angular position of this hole 56 relative to this groove 23, the cross section of said conduit passing through the device 1, and thus vary the flowrate obtained.

The ribs 35a to 35d and the bosses 15 are formed in such a way that, when the bosses 15 are engaged in the channels delimited by these ribs 35a to 35d, the components 2 and 3 clamp the member 4 between them. These ribs 35a to 35d and these bosses 15 thus make it possible to obtain the required sealing between these components 2 and 3.

When the bosses 15 are situated in the zones 36a to 36c, the component 3 can move axially with respect to the component 2, between the operating position of the device 1, in which the components 2 and 3 clamp the member 4 between them, and a sterilizing position, in which the stress exerted on this member 4 by the components 2 and 3 is relaxed.

The inclined walls 15a of the bosses 15 makes it possible to easily re-engage the bosses 15 in the channels delimited by the ribs 35a to 35d and to easily recompress the member 4 when one wishes to change from the sterilizing position to the operating position.

Figure 7:
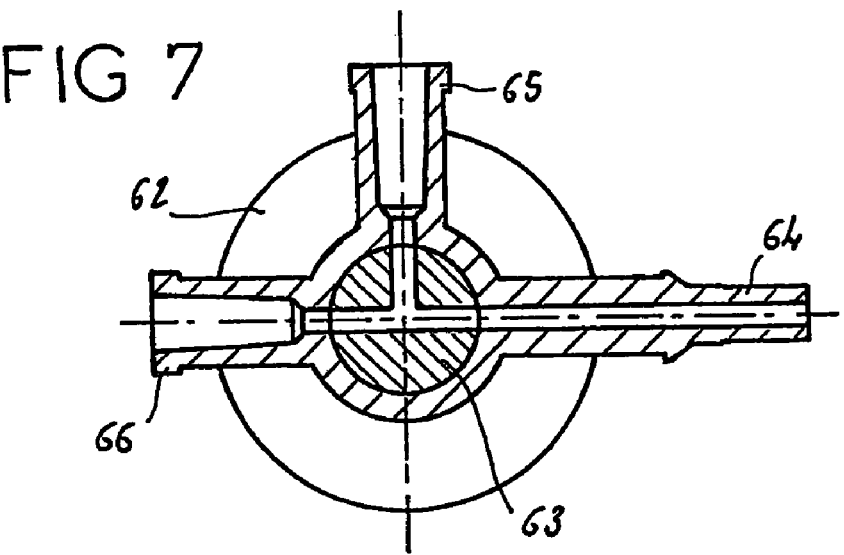
FIGS. 7 and 8 show a three-way valve in transverse section and longitudinal section, respectively.
Figure 8:
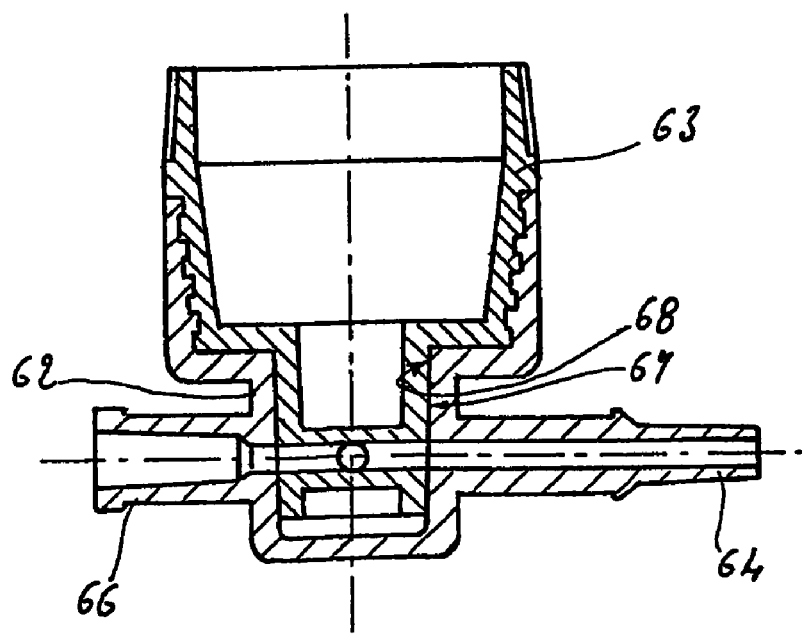

FIGS. 7 and 8 show a three-way valve comprising a body 62 in which a plug 63 is mounted. Three tubes (64, 65, 66) open out at the center of the body and are used to assemble three nozzles (not shown in the drawing). The sealing between the body 62 and the plug 63 is obtained by conical surfaces 67, 68 belonging, respectively, to the body and to the plug, and bearing against one another. The structure allowing the plug to be changed from the sterilizing position to the operating position is the same as before and is not described here.

As will be apparent from the foregoing, the invention brings a decisive improvement to the prior art by making available a flowrate control device for medical use which can be sterilized by means of steam, provides perfect sealing and has an optimized structure from the point of view of its manufacture.

It will be appreciated that the invention is not limited to the embodiments described above by way of example, and that instead it encompasses all alternative embodiments coming within the scope of protection defined by the attached claims.

The invention claimed is:

1. A flowrate control device (1), in particular for medical use, comprising two components (2, 3) connected to one another with possibility of displacement of one component relative to the other, sealing means placed between these two components (2, 3), and flowrate control means (23, 56) actuated by the displacement of one component (2, 3) relative to the other;

said device (1) being characterized in that it comprises positioning means (15, 35a to 35d, 36a to 36c) allowing the two components (2, 3) to be placed in two different positions, without disconnecting the two components (2, 3), namely a first position, called the "sterilizing" position, in which these two components (2, 3) do not exert, or hardly exert, any stresses on the sealing means, and a second position, called the "operating" position, in which these two components (2, 3) stress the sealing means (4) in such a way as to obtain the required sealing.

2. The device as claimed in claim 1, characterized in that the positioning means comprise:
   at least one groove formed in one of said components;
   at least one boss integral with the other component and sliding in this groove in order to permit displacement of the components relative to one another; and
   at least one clearance communicating with the groove, in which clearance the boss can be engaged in order to permit displacement of the component comprising the groove relative to the component comprising the boss, from said operating position to said sterilizing position, and vice versa.

3. The device as claimed in claim 2, characterized in that each groove and/or each boss has inclined zones forming ramps, these ramps facilitating the movement of the components from the sterilizing position to the position counter to the elastic restoring force of the sealing means.

4. The device as claimed in claim 2, characterized in that the groove has at least one entry in which a boss can be engaged in a defined position of one component relative to the other, and in that one of the components comprises at least one immobilizing catch, while the other component comprises at least one corresponding immobilizing catch, these catches being configured in such a way that the catch or catches of one component can snap in beyond the catch or catches of the other component during the first displacement of one component relative to the other and can then be immobilized beyond these in such a way as to prevent any return of the components to the position in which each boss is situated opposite each entry.

5. The device as claimed in claim 1, characterized in that the sealing means placed between the two component are formed by a separate sealing member.

6. The devices as claimed in claim 5, characterized in that the sealing member has a sealing portion with a U-shaped cross section, and in that said components have shapes which are such that, when they are joined together, they enclose this sealing portion from all directions.

7. The devices as claimed in claim 5, characterized in that said components are connected pivotably to one another, and in that one of the components delimits a conduit intended to be connected to a source of fluid, while the other component delimits a conduit intended to be connected to a tube for delivery of said fluid; one of said components comprises a wall in which there is formed, coaxially with respect to the axis of pivoting of one component relative to the other, a circular groove which extends along slightly less than one turn and has a variable depth along its length, and the conduit formed in this component opens into this grooves; the other component is integral in rotation with the sealing member which has an orifice communicating on the one hand with the conduit of this other component and on the other hand with said circular groove; the pivoting of this other component relative to the first component mentioned permits displacement of the orifice of the sealing member along the groove and, consequently, on account of the different depth of this groove at different locations thereof, permits variation of the cross section of the fluid delivery conduit depending on the angular position of one component relative to the other.

8. The device as claimed in claim 1, characterized in that one of said components comprises at least one slot opening to the outside, and in that the other of said components is integral in rotation with a ring which comprises data relating to the flowrate controlled by means of the device, said data coming into line with said slot in the different angular positions of the components, integral with the rings, relative to the component, comprising the slot.

9. The device as claimed in claim 1, characterized in that the sealing means are formed by two complementary conical surfaces which bear against one another and belong respectively to the components.

* * * * *